United States Patent [19]

Cook et al.

[11] Patent Number: 5,178,621
[45] Date of Patent: Jan. 12, 1993

[54] TWO-PIECE RADIO-TRANSPARENT PROXIMAL TARGETING DEVICE FOR A LOCKING INTRAMEDULLARY NAIL

[75] Inventors: Kevin S. Cook, Warsaw; Carl D. Ousley, Leesburg, both of Ind.

[73] Assignee: Zimmer, Inc., Warsaw, Ind.

[21] Appl. No.: 804,646

[22] Filed: Dec. 10, 1991

[51] Int. Cl.⁵ ............................................. A61B 17/56
[52] U.S. Cl. ..................................... 606/96; 606/97; 606/104
[58] Field of Search ................................. 606/96–98, 606/102, 104, 63

[56] References Cited

U.S. PATENT DOCUMENTS

| | | | |
|---|---|---|---|
| 4,570,624 | 2/1986 | Wu | 606/96 |
| 4,805,607 | 2/1989 | Engelhardt et al. | 606/64 X |
| 4,881,535 | 11/1989 | Sohngen | 606/98 |
| 4,911,153 | 3/1990 | Border | 606/98 |
| 4,978,351 | 12/1990 | Rozas | 606/96 X |

*Primary Examiner*—Robert A. Hafer
*Assistant Examiner*—Sam Rimell
*Attorney, Agent, or Firm*—Todd A. Dawson

[57] ABSTRACT

The targeting device of this invention includes a radio-transparent handle and a metal snap fit barrel. The radio-transparent handle reduces obstructions in the radio-graphic image to provide a clearer image to the surgeon for proper placement of the locking screws. The metal snap fit barrel is retained in the handle by an interference fit between the handle and biased keys carried by the barrel. After use, the barrel may be easily disassembled for cleaning by striking a removal tool against the keys to drive the barrel from the handle.

3 Claims, 1 Drawing Sheet

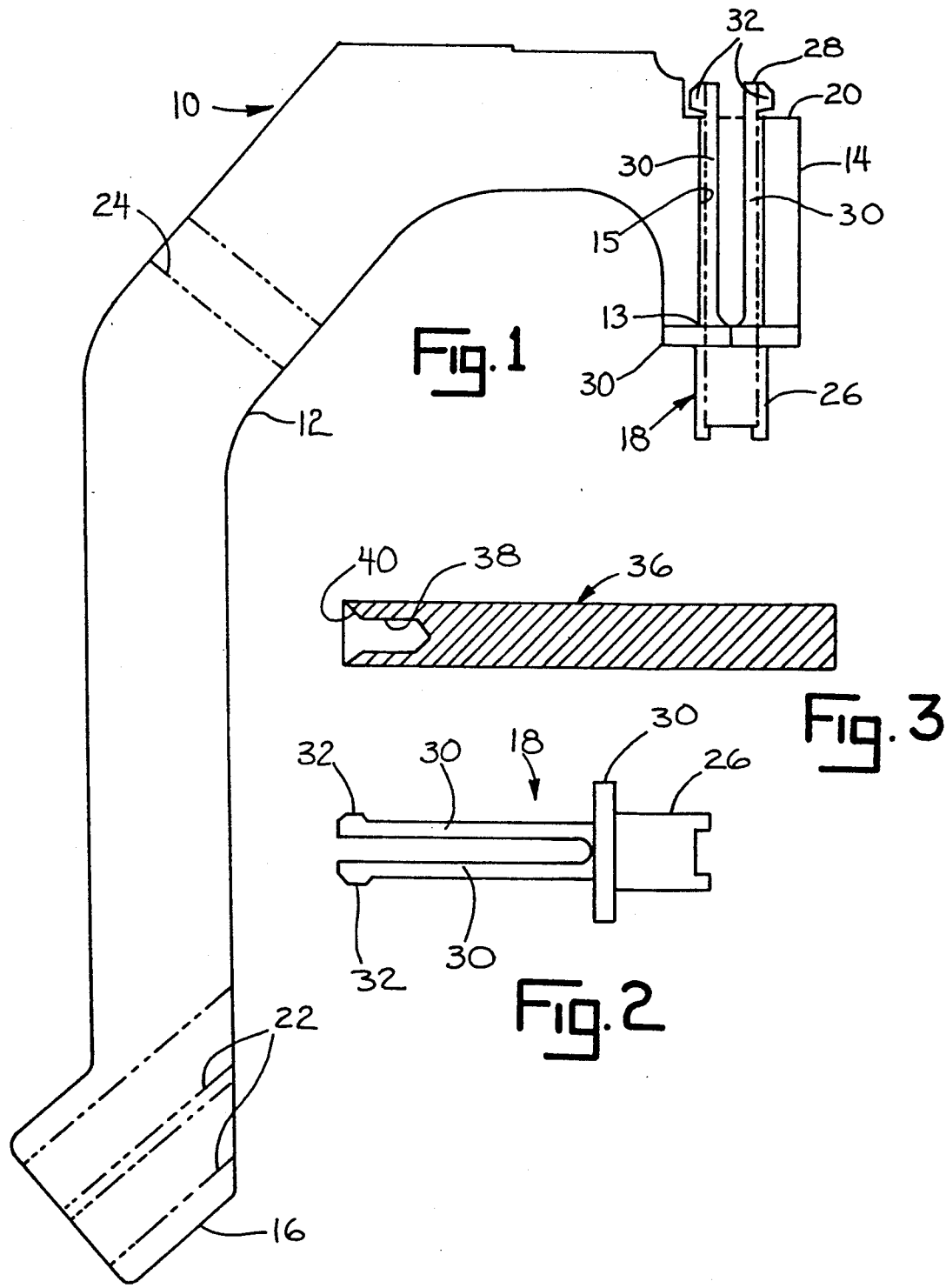

TWO-PIECE RADIO-TRANSPARENT PROXIMAL TARGETING DEVICE FOR A LOCKING INTRAMEDULLARY NAIL

BACKGROUND OF THE INVENTION

This invention relates to a proximal targeting device for a locking intramedullary nail as used in orthopedic fracture fixation.

BACKGROUND OF THE INVENTION

Locking intramedullary nails are used by orthopedic surgeons to secure a fracture of a long bone such as a femur. After insertion of the nail, a plurality of screws are driven through the bone and nail transverse to the longitudinal axis of the nail. To align the screw with transverse openings in the nail, a targeting device is attached to the proximal portion of the nail. It is typical for radio graphic pictures to be required during the procedure to ensure alignment of screws prior to drilling through the bone.

SUMMARY OF THE INVENTION

The targeting device of this invention includes a radio-transparent handle and a metal snap fit barrel. The radio-transparent handle reduces obstructions in the radio-graphic image to provide a clearer image to the surgeon for proper placement of the locking screws. The metal snap fit barrel is retained in the handle by an interference fit between the handle and biased keys carried by the barrel. After use, the barrel may be easily disassembled for cleaning by striking a removal tool against the keys to drive the barrel from the handle.

Accordingly, it is an object of the invention to provide for a novel targeting device for a locking intramedullary rod.

Another object of the invention is to provide for a novel two piece targeting device for an intramedullary nail.

Another object of the invention is to provide for a targeting device for an intramedullary nail having a radio-transparent handle.

Still another object of the invention is to provide for a targeting device for an intramedullary nail which is easily disassembled for cleaning.

Yet another object of the invention is to provide for a targeting device for an intramedullary nail that is economic to produce.

Further objects of the invention will become apparent upon a reading of the following description taken with the accompanying drawings.

BRIEF DESCRIPTION OF THE DRAWINGS

FIG. 1 is a elevational view of the targeting device of the invention.

FIG. 2 is an elevational view of the metal guide barrel of the invention.

FIG. 3 is a sectional view of the guide barrel removal tool.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Referring now to the figures, targeting device 10 is illustrated as including a handle 12 formed from a radio-transparent plastic material. As illustrated in the figures, handle 12 is generally C-shaped and includes a rod engaging end 14 and a targeting end 16. Rod engaging end 14 includes a throughbore 15 for accommodating the guide barrel 18. A recess is formed in rod engaging end 14 defining shoulders 20. Throughbores 22 are formed through targeting end 16 for accommodating a drill bushing (not shown) for drilling into a patient's bone to accommodate a locking screw (also not shown). A throughbore 24 is formed through handle 12 at a location between throughbores 15 and 22. Throughbores 22 and 24 are oriented such that with the handle 12 and guide barrel 18 contacting the proximal end of an intramedullary (IM) nail (not shown), a drill bit passing through bores 22 and 24 would mate with corresponding bores in the IM nail. This feature is common with many targeting guides and is not to be considered unique to this invention.

Guide barrel 18 is generally of a tubular cross section and includes a distal end 26 and a proximal end 28 divided by a collar 30. The distal end 26 of barrel 18 includes a pair of protrusions for mating with corresponding notches on the proximal end of the IM nail. The proximal end 28 of the barrel is slotted to define a pair of spring arms 30. Each spring arm 30 terminates in an arcuate lip 32 extending transversely from arms 30. The proximal most edge of each lip 32 is bevelled to form a caming surface.

To connect guide barrel 18 with handle 12 for use, the proximal end 28 of barrel 18 is placed in contact with the distal opening 13 of throughbore 15. Axial pressure is applied to the guide barrel, the bevelled surfaces of lips 32 contact the handle about opening 13 which causes the spring arms to cam inwardly toward each other. Continued axial pressure causes the proximal end 28 of guide barrel 18 to travel along bore 15. When lips 32 pass through bore 15 and reach the recess, the arms spring outwardly such that lips 32 overly the shoulders 20 to secure the barrel against longitudinal movement relative to handle 12. The targeting device may now engage an IM rod to provide alignment in a manner well known in the industry. A locking bolt (not shown) may be inserted through the center of tubular guide rod 18 to secure the targeting guide to the IM rod.

During the procedure, it may be necessary to obtain radiographic images such as X-rays. Since the handle of the invention is formed from a radio-transparent material, the targeting guide may be left connected to the IM rod without significantly obstructing the image.

After the procedure, it is necessary to remove the guide barrel 18 for cleaning of the handle and guide barrel. A removal tool 36 is provide as illustrated in FIG. 3. Removal tool 36 includes a cylindrical rod having a blind bore 38 formed in one end thereof. Bore 38 includes a bevelled edge 40. The bevelled edge 40 of tool 36 is placed against the bevelled outer surface of lips 32. The exposed end of the removal tool is struck with mallet. The cooperating bevelled surfaces of the tool and the lips cams the spring arms together and drives the barrel into bore 15. The barrel may now be pulled from the bore for cleaning.

It should be understood that the exact location of the bores 22 and 24, as well as the shape of handle 12, is dependant on the particular configuration of the IM rod.

It should be further understood that the invention is not to be limited to the precise details above but may be modified within the scope of the appended claims.

We claim:

1. A targeting device for connection to the proximal end of an intramedullary nail for aligning a boring device with transverse bores of an intramedullary nail when the nail is seated within a intramedullary canal of a patient, said targeting device including a handle member and a guide barrel adapter for engagement with the proximal end of the intramedullary nail adjacent a central longitudinal bore of the intramedullary nail, said handle member including a plurality of openings therethrough constituting guide bores, the guide barrel being removably carried within a through bore of said handle member such that said guide barrel is substantially longitudinally aligned with the central bore of the intramedullary nail and contacts a proximal end of the intramedullary nail, said throughbore defining a shoulder on said handle, wherein said guide barrel includes a proximal end and a distal end, said proximal end including at least two arms extending generally parallel relative to each other, each of said arms terminating in a outwardly extending lip, said arms being biased apart, said lips overlying said shoulder of said throughbore to removably connect the guide barrel to said handle for engagement with the proximal end of the intramedullary nail.

2. The targeting device of claim 1 wherein said arms are shiftable into a converging orientation such that said lips are capable of passing through said one of said openings in said handle to permit insertion or removal of said guide barrel.

3. The targeting device of claim 1 wherein each of said lips includes a beveled outer edge which constitutes caming surfaces to urge said arms into said converging orientation when force is exerted against said surfaces.

* * * * *